United States Patent [19]
Mosby

[11] Patent Number: 5,260,985
[45] Date of Patent: Nov. 9, 1993

[54] CONFORMING LOCALIZATION/BIOPSY GRID AND CONTROL APPARATUS

[76] Inventor: Richard A. Mosby, P.O. Box 20554, Houston, Tex. 77225

[21] Appl. No.: 931,757

[22] Filed: Aug. 14, 1992

[51] Int. Cl.⁵ .............................................. H05G 1/28
[52] U.S. Cl. .................................... 378/164; 378/37; 378/163; 378/208
[58] Field of Search ............... 378/162, 163, 164, 208, 378/204, 177, 179, 37; 604/44, 116, 117, 158, 164, 264, 272; 606/167, 170, 181, 185; 128/754

[56] References Cited

U.S. PATENT DOCUMENTS

| | | | |
|---|---|---|---|
| 3,547,121 | 12/1970 | Cherry | 378/164 |
| 3,706,883 | 12/1972 | McIntyre | 378/163 |
| 4,005,527 | 2/1977 | Wilson et al. | 378/163 |
| 4,319,136 | 3/1982 | Jinkins | 378/163 |
| 4,341,220 | 7/1982 | Perry | 378/162 |
| 4,582,061 | 4/1986 | Fry | 606/185 |
| 4,618,978 | 10/1986 | Cosman | 378/164 |
| 4,838,265 | 6/1989 | Cosman et al. | 378/164 |

FOREIGN PATENT DOCUMENTS

| | | | |
|---|---|---|---|
| 8801847 | 3/1988 | PCT Int'l Appl. | 378/208 |
| 0537677 | 12/1976 | U.S.S.R. | 606/185 |

*Primary Examiner*—David P. Porta
*Attorney, Agent, or Firm*—Neal J. Mosely

[57] ABSTRACT

A conforming biopsy grid and control apparatus consists of a flat transparent adhesive pliable sheet of material with imprinted radiopaque and visible grid lines which are numbered and lettered in more than one axis and applied to a structure. An adjustable perforated box-like apparatus is applied to stabilize compliant and/or elastic structures and placed about the grid applied structure fixing compliant and/or plastic structures tightly to conform to the shape of the box-like apparatus. A calibrated, perforated stylet is placed through the composite, i.e., compliant and/or elastic structure, conforming biopsy grid, and containing box-like apparatus, and stabilized by locking devices as it enters and exits the containing box-like apparatus. Electromagnetic and/or visible means are used to determine placement of this stylet through the perforated box-like apparatus to localize internal structures in more than one plane indicating location and depth of structures to be biopsied.

14 Claims, 4 Drawing Sheets

CONFORMING LOCALIZATION/BIOPSY GRID AND CONTROL APPARATUS

BACKGROUND OF THE INVENTION

1. Field of the Invention

This invention relates to localizing devices and more particularly to localizing devices that use external markers to assist in localization. This invention relates to stabilizing devices to control compliant and/or elastic structures. This invention has particular usefulness in medical and industrial applications.

2. Description of the Prior Art

Presently available localization devices use a grid apparatus which is firm and inflexible and indicates lesion or structure location information in only one plane requiring repositioning to obtain location information in any other plane. Other available localization devices and procedures use uncontrollable and variably reliable methods to attempt to induce accuracy such as vision, touch, consistency, assumption of position, and are used singly or in combination. These methods produce highly variable results with respect to accuracy. This results in repeat of biopsy, and exposes the patient to other medical problems such as excessive trauma to the structure, infection, excessive bleeding, excessive exposure to radiation, pneumothorax and others.

Localization devices have long been used in locating lesions or other area of interest within human parts. These consist of flat, firm plate-like material with calibrated markings and permeations fixed to a firm metallic control arm which compresses subject human body part against a firm plastic or metallic x-ray cassette held in place by a metallic cassette holding table. X-rays are taken to determine the relationship of the localizing device to the lesion or other area of interest within human body parts. A localizing device, such as a needle, is placed through the permeated grid into or near the lesion or other area of interest within human body parts and this placement is determined and guided by the relationship of the grid to the location of the lesion or other area of interest within the human body part. Another x-ray is obtained to determine accuracy of placement of the localizing device, such as a needle. Should placement be erroneous subsequent x-rays and subsequent localizing needle placements will be required until adequate placement results. This provides localization of lesions or other areas of interest in human body parts in only one plane. In order to determine other parameters of location, such as depth, compression of the human body part must be released and the entire localization device placed in a different plane and the entire procedure as indicated above must be repeated. The release of the compressed human body part at this time changes all relationships as determined by the previous localization and may allow the localization needle to move with reference to the lesion or other area of interest in human body parts and change previously determined parameters such as location of the localization needle tip to the lesion or other area of interest in human body parts. Repositioning of localization device, movement of the subject human body part, and replacement of the localization device distorts all reference points producing inconsistent and unreliable localization of lesions or other areas of interest within human body parts.

In mammography, the localization devices used are placed in one plane to determine location and in a separate plane to determine depth. The human breast is compliant and flexible and in the replacement of the localization device for the separate plane view, the human breast returns to its normal configuration and location allowing the initial plane localization to become inaccurate.

In industry, similar non conforming localization apparatus is also used and with complaint flexible structures similar errors in accuracy result.

The conforming localization/biopsy and control apparatus of this invention applies the grid display directly to the subject human body part and fixes compliant and flexible human body parts in a box-like apparatus to conform the human body part to the shape of the box-like apparatus and thereby not allowing changes in the relationships of the lesion or other area of interest in human body parts to the grid display applied directly to the subject human body part during the obtaining of localization information in various planes by electromagnetic or visual means. A permeated calibrated control stylet is introduced into the permeated box-like apparatus and completely through subject human body part, lesion and/or other area of concern within human body parts and fixed at both sides of the box-like apparatus by locks to give a consistent indication of the depth and/or location of the lesion or other area of interest within human body parts in subsequent and various planes using electromagnetic or visual means. In comparison to presently available localizing devices, the conforming localizing/biopsy grid and control apparatus provides consistent and fixed relationships between all units of the composite producing accurate and consistently reliable localization of lesions or other areas of interest within human body parts.

In mammography, the standard localization devices are inflexible and require repositioning to establish relationships and parameters. This repositioning results in movement of structures internal to the breast thereby changing previously determined parameters and relationships in one plane while attempting to determine parameters and relationships in a different plane. The conforming biopsy grid and control apparatus of this invention fixes all relationships and parameters by applying a conforming, flat, pliable sheet with a grid display, visible to electromagnetic and visual means, variably numbered and lettered, to the outside of the human breast. The human breast with the conforming grid sheet applied is placed into an adjustable perforatee box-like apparatus conforming the human breast with applied conforming grid sheet to the shape of the confining adjustable perforated box-like apparatus, thereby, fixing all relationships and parameters of the composite and not allowing movement of the human breast. After noting the relationship of a lesion or other area of interest in human body parts by electromagnetic or visual means to the conforming grid, a perforated calibrated stylet visible to electromagnetic and visual means is placed through the composite in or adjacent the lesion or other area of concern within human body parts and exposes both of its ends which are locked in place on both sides of the adjustable perforated apparatus to prevent movement. X-rays are taken of the composite in various planes as needed to determine location and depth of a lesion or other area of concern in human body parts without concern for changes in relationships or parameters inherent in the movement of subject human body part in obtaining x-rays in various or subsequent planes. X-rays showing the human breast, conforming grid, box-like apparatus and fixed control stylet are used to place a localization device, such as a needle, accurately into or adjacent to a lesion or other area of interest in human body parts by inserting the needle through or adjacent to the permeated calibrated control stylet to the depth indicated on the x-ray view of the markings of the calibrated stylet at The depth of the lesion or other area of interest in human body parts. The localizing needle is secured by a barb near its tip and the composite of the conforming biopsy grid and control apparatus is removed for surgical biopsy or biopsy is performed using standard techniques while the composite is in place.

The localization requires the use of x-rays in two planes reducing radiation exposure. One plane for the insertion of the control stylet and one to determine depth of the lesion or other area of interest within human body parts.

In industrial uses, standard localization devices do not conform to the subject. The conforming localization/biopsy grid and control apparatus conform to subject outline and electromagnetic or visual means are used to determine location and depth of structures of concern within subject structure.

SUMMARY OF THE INVENTION

One object of this invention is to provide a localization device and procedure that fixes and controls all relationships and parameters using the subject structure as a standard reference by applying a flat, transparent, adhesive, pliable sheet of material with imprinted radiopaque and visible grid lines which are numbered and lettered in more than one axis to subject structure.

It is another object of this invention is to provide a localization device and procedure that fixes and controls all relationships and parameters using an external apparatus to prevent changes in relationships and parameters by placing subject structure with applied pliable grid into an adjustable, perforated box-like apparatus conforming compliant and/or flexible structures to the shape of the box-like apparatus preventing movement.

Another object of this invention is to provide a localization device and procedure that fixes and controls all relationships and parameters using a calibrated linear marker that employs a calibrated perforated stylet placed through the composite of the box-like apparatus, conforming grid, subject structure and identified lesion or other area of interest in human body parts or other structures being locked in place at each exposed end on either side of the box-like apparatus allowing determination of location and depth of a lesion or other area of interest in human body parts or other structures by exposure to electromagnetic, i.e., x-ray or visual means, in various planes of evaluation.

Another object of this invention is to provide a localization device and procedure that improves accuracy and reliability of localization by allowing complete localization utilizing a maximum of two planes of evaluation.

Another object of this invention is to provide a localization device and procedure that limits exposure of subject body part to electromagnetic radiation such as x-rays, by decreasing the number of x-ray exposures required to insure accuracy and reliability of the localizing.

Another object of this invention is to provide a localization device and procedure that minimizes medical complications of localizations such as bleeding, infection, pneumothorax, etc by improving accuracy and reliability thereby eliminating need for additional localization device, such as a needle, manipulation.

Other objects of the invention will become apparent from time to time throughout the specification and claims as hereinafter related.

These and other objects of the invention are accomplished by a new and improved localization device and procedure which consists of an adherent flat transparent sheet with grid markings and identifying numbers and letters visible to electromagnetic and visual means applied to a human body structure submitted for localization of a lesion internal to that structure. The human body structure with conforming grid sheet applied is placed within an adjustable permeated box-like apparatus conforming the human body structure to that of the confining box-like apparatus. X-rays are taken in the vertical plane to determine the relationship of a lesion or other area of interest in human body parts to the applied grid sheet. After determining the relationship to the lesion, a perforated calibrated control stylet is placed vertically through perforation in the box-like apparatus above the grid lines closest to the lesion and inserted completely through the box-like apparatus in a vertical orientation to pass out the inferior corresponding perforation. The perforated calibrated control stylet is then locked into place superiorly and inferiorly as to prevent its movement. An x-ray is taken in the horizontal plane to determine depth of the lesion as indicated by the markings on the control stylet and its relationship to the adherent grid sheet. A localizing needle or biopsy needle is placed through or adjacent to the permeated calibrated control stylet and localization is performed by fixing the localization needle in place or performing a needle biopsy by extending them to the previously determined depth indicated by the stylet markings and/or conforming grid sheet markings.

DESCRIPTION OF THE PREFERRED EMBODIMENT

The conforming localization/biopsy grid and control apparatus represents a localization device and procedure comprising a flat transparent adhesive sheet of material with imprinted radiopaque and visible grid lines which are numbered and lettered in more than one axis and applied to subject structure. An adjustable perforated box-like apparatus is employed to fix and immobilize compliant and flexible structures to prevent change in relationships or parameters of structures internal to the subject structure. A vertical x ray is taken to determine the relationship of a mass or structure of interest to the conforming grid sheet. A permeated calibrated control stylet is placed into and through the box-like apparatus in perforations corresponding to the location of a mass or structure of interest as determined by the x-ray grid pattern and is secured by locks at the superior and inferior exposure of its ends. A horizontal x-ray is then taken to determine the depth of the mass or structure of interest as indicated by the markings of the control stylet and conforming grid sheet. A localization or biopsy needle is then placed through or adjacent to the control stylet to the depth and location indicated by the calibration markings and the conforming grid sheet. Localization by securing the localization needle by extending a barb at the tip or securing to the subject structure by tape or securing suture is then obtained. Biopsy by needle manipulation or aspiration may also be obtained. The general purpose is to improve accuracy and reliability in localization of masses or structures of interest internal to subject structure. The specific purpose is to use the subject structure as a standard reference instead of extraneous apparatus. For example in mammography, the human breast is compliant and flexible. Extraneous apparatus used for localization becomes inaccurate in the required movement to evaluate different planes. This invention fixes and controls movement of compliant flexible breast tissue at all times and in all planes.

Figure 1:
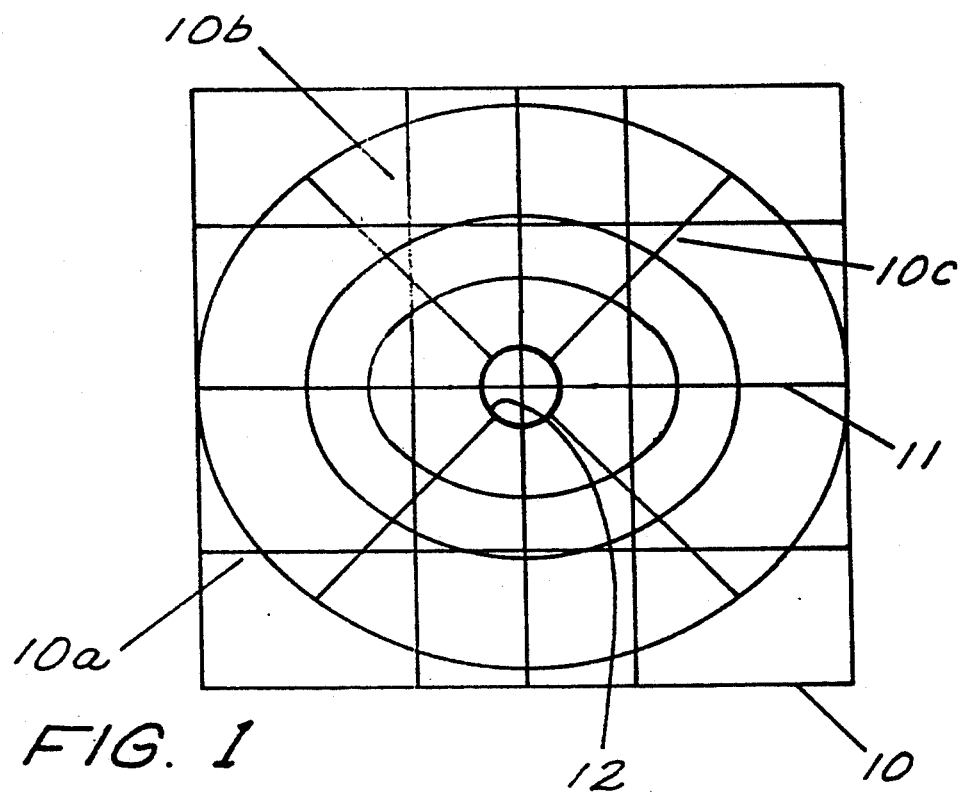
FIG. 1 shows a view of a flat transparent sheet with circular and horizontal grid pattern, numbered to define quadrants with a central hole for placement of the nipple of a human breast.

FIG. 1 shows a view of the conforming grid sheet flat with vertical, horizontal and oblique numbered lines, G, AND nipple exposure hole, N.

Figure 2:
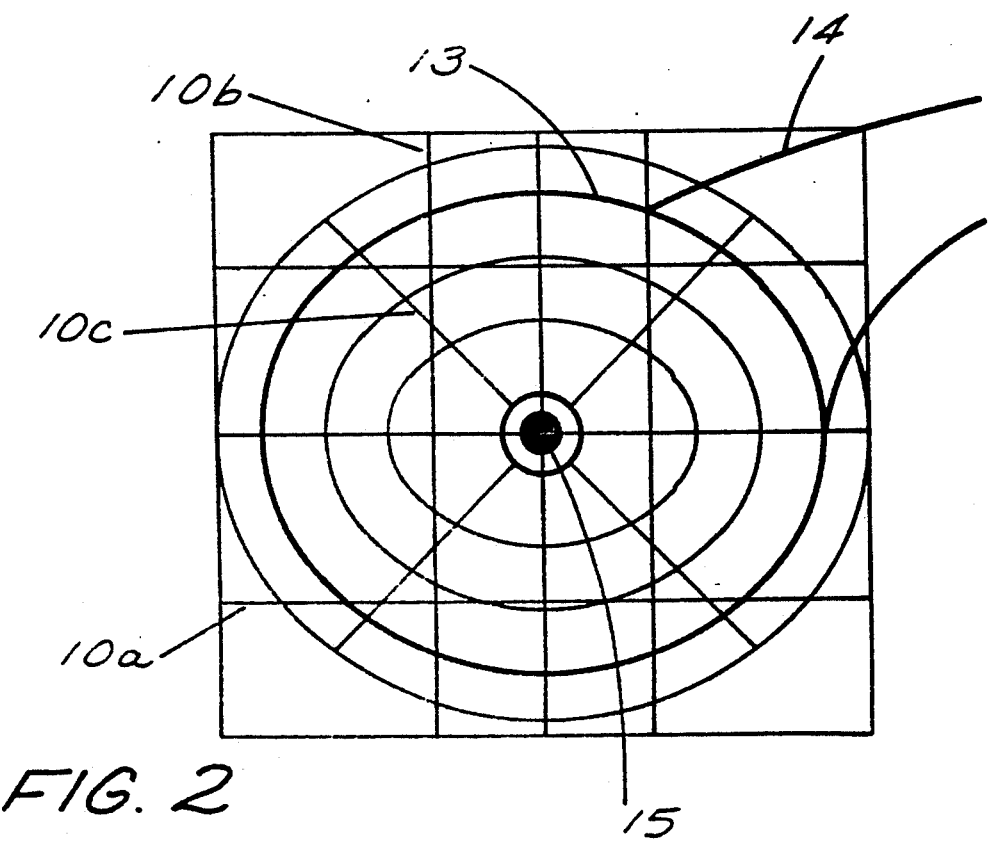
FIG. 2 shows the flat transparent grid sheet applied to a human breast to conform to the breast and axillary tail with nipple exposed through central hole.

FIG. 2 shows a view of the conforming grid sheet adhered and conforming to the outline of human breast and axillary slip with horizontal, vertical and oblique numbered lines in grid pattern, G, human breast, B, axillary slip, R, and exposed breast nipple in central hole, N.

Figure 3:
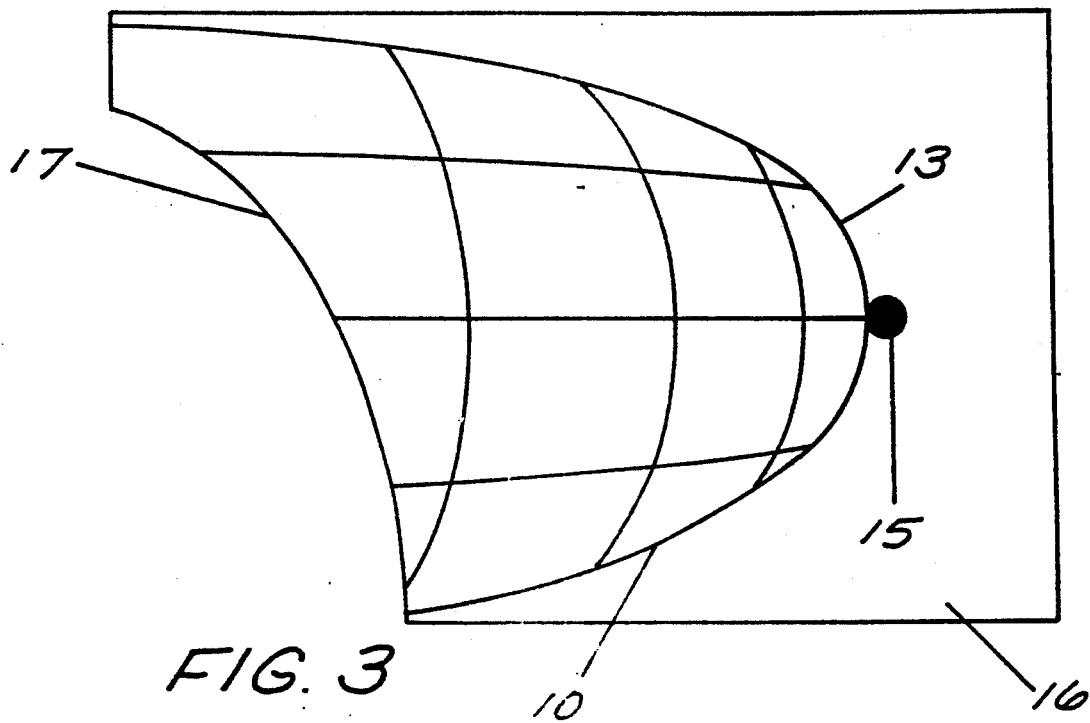
FIG. 3 shows the flat transparent grid sheet applied to and conforming to a human breast seen in a vertical plane over an x-ray cassette.

FIG. 3 shows a vertical view of the conforming grid applied to the human breast with numbered vertical and horizontal lines with conforming grid, G, nipple exposed through central hole, N, on an x-ray cassette, C, with contoured margin, A.

Figure 4:
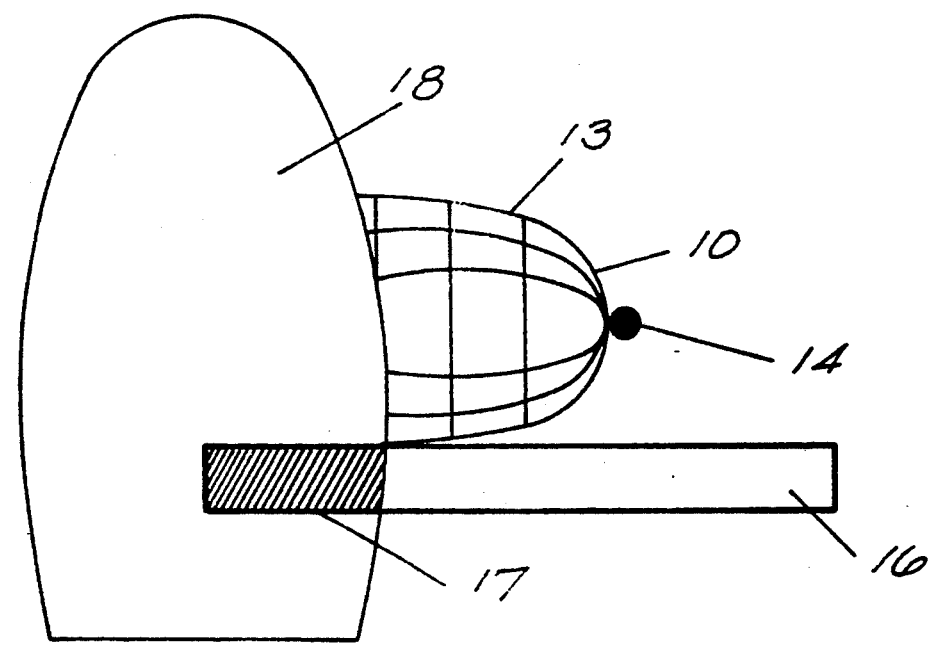
FIG. 4 shows the transparent grid sheet applied to and conforming to the outline of a human breast and above an x-ray cassette in the horizontal plane.

FIG. 4 shows a horizontal view of the conforming grid applied to the human breast with numbered vertical and horizontal grid lines with conforming grid, G, nipple exposed through central hole, N, above an x-ray cassette, C, with contoured edge, A, against chest wall, T.

Figure 5:
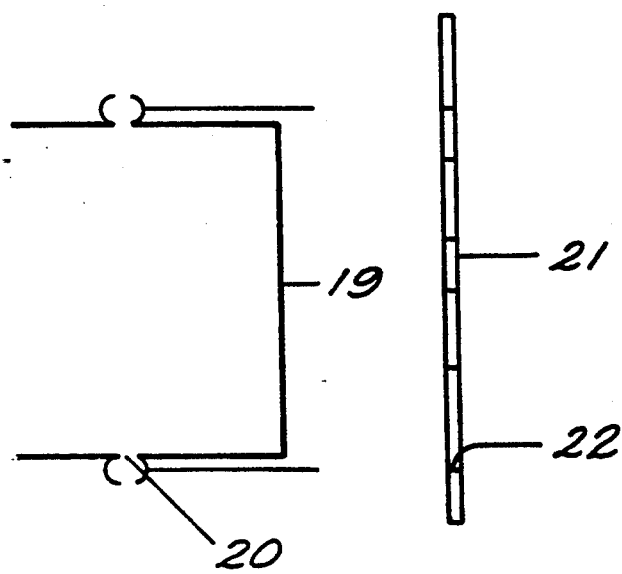
FIG. 5 shows the adjustable perforated box-like apparatus with perforated calibrated control stylet in a side view.

FIG. 5 shows a side view of the adjustable perforated box-like apparatus and perforated calibrated control stylet with box-like apparatus, X, locking perforation, L, and calibrated stylet, S.

Figure 6:
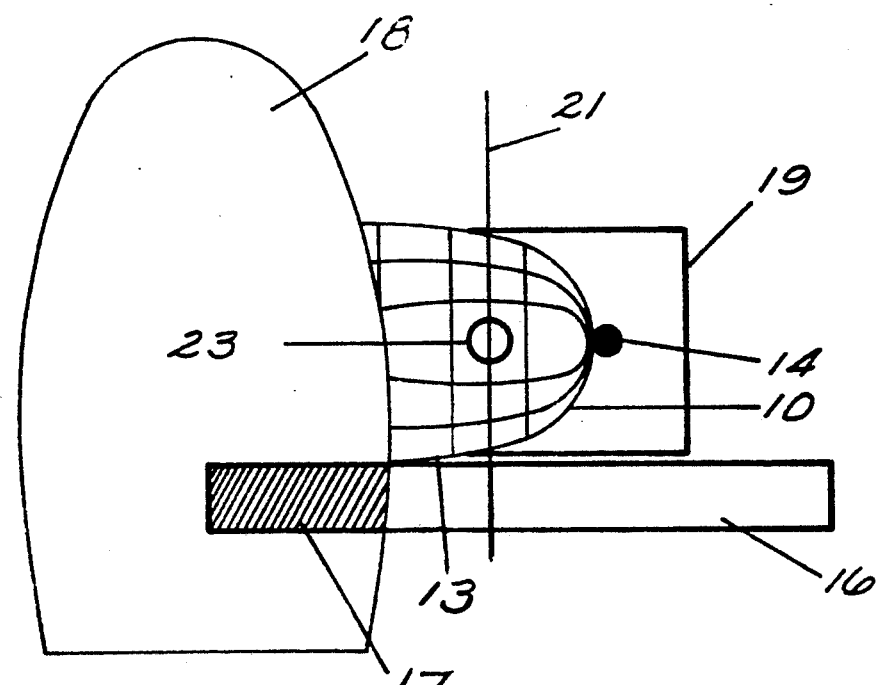
FIG. 6 shows the adjustable perforated box-like apparatus with permeated calibrated stylet vertically inserted with superior and inferior ends exposed and locked in place at these exposed ends.

FIG. 6 shows a side view of the entire apparatus as used in a functional composite with conforming grid sheet, G, applied to the human breast nipple exposed through central hole, N, with the perforated box-like apparatus, X, confining the human breast and control stylet, S, placed through the composite into or near a mass, Z, the breast supported by an x-ray cassette, C, contoured at, a, against chest wall, T.

Figure 7:
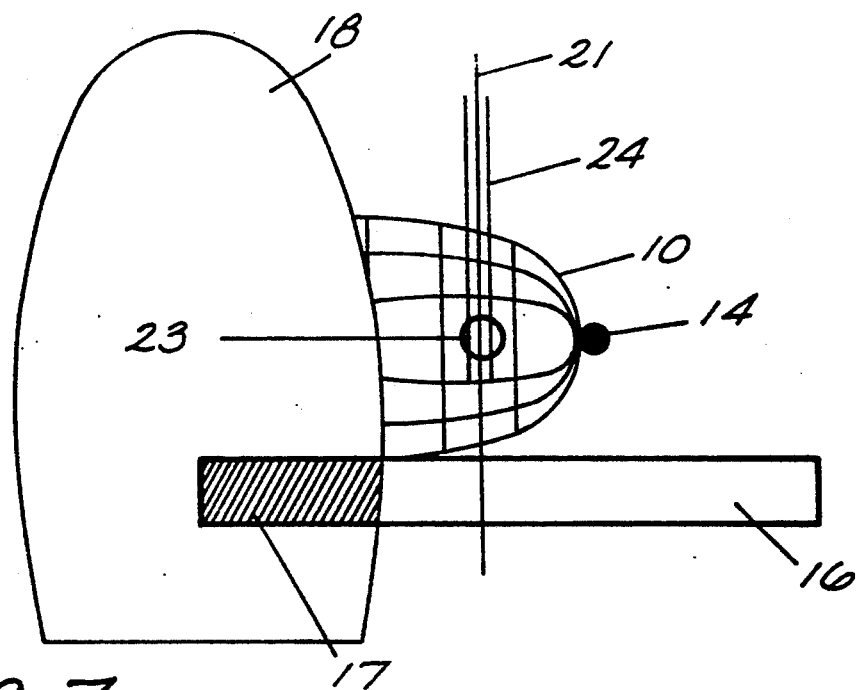
FIG. 7 shows placement of a localizing or biopsy needle through or adjacent to the permeated calibrated control stylet to the level of a mass. Box-like apparatus removed to demonstrate.

FIG. 7 shows a side view of the device with box-like apparatus removed to demonstrate placement of a localizing or biopsy needle, K, adjacent or through the control stylet, S, to the depth of the mass, Z, to be secured, with conforming grid, G, applied to breast with nipple exposed through central hole, N, with breast supported by an x-ray cassette, C, contoured at, A, and placed against chest, T.

Figure 8:
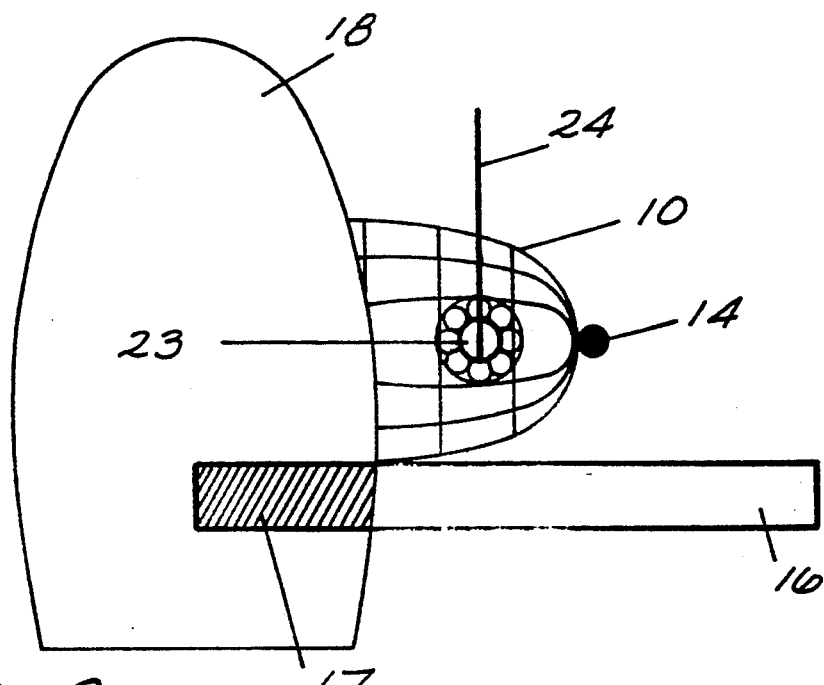
FIG. 8 shows placement and securing of localization or biopsy needle in area of mass. Box-like apparatus and control stylet removed.

FIG. 8 shows a side view of the human breast with localizing or biopsy needle, K, secured in mass, Z, for localization or biopsy with conforming grid, G, applied with nipple exposed through central hold, N, supported by an X-ray cassette, C, contoured at, A, against chest, T.

The various parts of the device are used in concert to assist in the use of the subject object as a standard reference for localization of lesions internal to subject structure. FIGS. 2, 3 and 4 show how the conforming grid sheet, G, is applied, in this instance to the human breast, to make the human breast serve as its own standard reference. FIG. 6 shows how the perforated, adjustable box-like apparatus is applied to fix and confine the compliant and flexible breast to preclude any charge in the grid/breast relationship while placing and locking the perforated calibrated control stylet to assist in determining depth and location of masses internal to any structure. FIG. 7 shows how the localization or biopsy needle is inserted to the level of the mass, adjacent or through the perforated control stylet.

The conforming grid is constructed of pliable compliant plastic, paper or other durable thin sheet-like material that allow marking with radiopaque and visible lines, letters and numbers. The prime feature is that it conform to the outline of subject structure. The purpose of this conforming is to allow subject structure to become its own standard reference. As example, in FIGS. 1, 2, 3, and 4 the conforming grid, g, adheres and conforms to the outline of subject breast making the breast its own standard reference for lesions internal to it.

The perforated adjustable box-like apparatus, x, is constructed of plastic, metal or other durable material transparent to electromagnetic radiation. The prime feature is that it becomes a confining structure for compliant and flexible structures and human body parts. The purpose of this confining is to fix the compliant and flexible structures or human body parts to prevent movement, thereby, maintaining all relationships and parameters provided by the conforming grid sheet, g,. For example, in FIG. 6, the perforated adjustable box-like apparatus is shown applied and adjusted to conform the breast to the shape of the box-like apparatus, x,. This prevents movement during the evaluation of the composite in all planes.

The perforated calibrated control stylet, s, is constructed of metal, plastic or other durable materials and is linear. The prime feature is to fix the defined mass, z, in the breast for depth and location in subsequent plane evaluation. The purpose is to fix and preclude movement of the mass, z, in subsequent plane evaluations and serve as a guide for the localization or biopsy needle, k, as it descends to the depth of the identified mass, Z, for localization or biopsy. For example, in FIGS. 6 and 7 the stylet, s, is placed through the composite of the device and the identified mass and locked at top and bottom, l, (FIG. 5) to insure relationships and parameters are not disturbed while depth and lateral location is determined. The stylet is used as a guide for placement of the localization or biopsy needle, k, through or adjacent to the stylet by placing the localization or biopsy needle through or adjacent to the stylet.

In the various views a conforming localization device is shown which consists of a conforming grid sheet, confining and fixing box-like apparatus and a control stylet all of which assist subject structure to become its own standard reference while preventing any change in relationships or parameters by not allowing any motility of the standard reference structure. This standard reference composite improves and insures accurate, consistent and reliable localization of lesions or other area of interest in human body parts for the purpose of localization of biopsy.

In FIG. 8, there is shown a mass, z, localized for localization or biopsy with localization or biopsy needle Tip, K, within the mass, Z, with conforming grid sheet, G, applied to the outline of the breast.

While this invention has been shown fully and completely with special emphasis on certain preferred embodiments, it should be understood that within the scope of the appended claims the invention may be practiced otherwise than as specifically described herein.

I claim:

1. A method of localizing body masses and controlling biopsy or biopsy surgery which comprises
   (a) providing a thin flexible sheet material sufficiently compliant to conform to a body surface being evaluated and having an adhesive backing for uniform securing to said body surface and a plurality of grid lines and indicia thereon of a material opaque to detectable electromagnetic radiation and to visible light,
   (b) adhering said sheet uniformly to a body surface having a pronounced bulge to cover the entire surface, and
   (c) examining said body surface by detectable electromagnetic radiation in at least two different planes, to produce images which localize a body mass in different planes by position coordinates by reference to said grid lines.

2. A method of localizing body masses and controlling biopsy or biopsy surgery according to claim 1 in which
   biopsy or biopsy surgery is carried out subsequent to said body surface examination with reference to the position coordinates obtained.

3. A method of localizing body masses and controlling biopsy or biopsy surgery according to claim 1 including the step of
   obtaining a mammogram subsequent to said body surface examination with reference to the position coordinates obtained.

4. A method of localizing body masses and controlling biopsy or biopsy surgery according to claim 1 including the steps of
   providing a box-like apparatus with walls on four sides of durable material transparent to said electromagnetic radiation, and openings on two opposing sides, and perforated by holes on all walled sides, and
   applying said box-like apparatus over said grid sheet to hold the same in position against motion.

5. A method of localizing body masses and controlling biopsy or biopsy surgery according to claim 1 including the steps of
   providing a box-like apparatus with walls on four sides of durable material transparent to said electromagnetic radiation, and openings on two opposing sides, and perforated by holes on all walled sides, and
   applying said box-like apparatus over said grid sheet to hold the same in position against motion, and
   performing biopsy or biopsy surgery subsequent to said body surface examination with reference to the position coordinates obtained.

6. A method of localizing body masses and controlling biopsy or biopsy surgery according to claim 1 including the steps of
   providing a linear hollow stylet of material opaque to electromagnetic radiation and visible to light, having calibrating markings throughout the entire length, and perforated laterally to permit passage of a biopsy needle, and
   inserting said stylet through said body surface covered with said grid sheet, whereby the examination of said body surface by electromagnetic radiation in at least two different planes, whereby the pictures produced localize a body mass by position coordinates by reference to said grid lines in different planes and in reference to said stylet.

7. A method of localizing body masses and controlling biopsy or biopsy surgery according to claim 1 including the steps of
   providing a linear hollow stylet of material opaque to electromagnetic radiation and visible to light, having calibrating markings throughout the entire length, and perforated laterally to permit passage of a biopsy needle, and
   inserting said stylet through said body surface covered with said grid sheet, whereby the examination of said body surface by electromagnetic radiation in at least two different planes,
   whereby the pictures produced localize a body mass by position coordinates by reference to said grid lines in different planes and in reference to said stylet, and
   performing biopsy or biopsy surgery subsequent to said body surface examination with reference to the position coordinates obtained.

8. A method of localizing body masses and controlling biopsy or biopsy surgery according to claim 1 including the steps of
   providing a box-like apparatus with walls on four sides of durable material transparent to said electromagnetic radiation, and openings on two opposing sides, and perforated by holes on all walled sides,
   applying said box-like apparatus over said grid sheet to hold the same in position against motion,
   providing a linear hollow stylet of material opaque to electromagnetic radiation and visible to light, having calibrating markings throughout the entire length, and perforated laterally to permit passage of a biopsy needle, and
   inserting said stylet through perforations in said box-like apparatus said body surface covered with said grid sheet to visually locate the position of said stylet, whereby the examination of said body surface by electromagnetic radiation in at least two different planes, produces pictures which localize a body mass by position coordinates by reference to said grid lines in different planes and in reference to said stylet, and performing biopsy or biopsy surgery subsequent to said body surface examination with reference to the position coordinates obtained.

9. A method of localizing body masses and controlling biopsy or biopsy surgery according to claim 8 including the steps of providing a biopsy needle and inserting it through one of said stylet perforations to place the needle accurately in relation to the body surface being examined.

10. A method of localizing body masses and controlling biopsy or biopsy surgery according to claim 1 including the steps of providing a box-like apparatus with walls on four sides of durable material transparent to said electromagnetic radiation, and openings on two opposing sides, and perforated by holes on all walled sides, applying said box-like apparatus over said grid sheet to hold the same in position against motion, providing a linear hollow stylet of material opaque to electromagnetic radiation and visible to light, having calibrating markings throughout the entire length, and perforated laterally to permit passage of a biopsy needle, and inserting said stylet through perforations in said box-like apparatus said body surface covered with said grid sheet to visually locate the position of said stylet, whereby the examination of said body surface by electromagnetic radiation in at least two different planes, produces pictures which localize a body mass by position coordinates by reference to said grid lines in different planes and in reference to said stylet, and obtaining a mammogram subsequent to said body surface examination with reference to the position coordinates obtained.

11. Apparatus for use in localizing body masses and controlling biopsy or biopsy surgery which comprises a thin flexible sheet material sufficiently compliant to conform to a body surface being evaluated and having an adhesive backing for uniform securing to said body surface and a plurality of grid lines and indicia thereon of a material opaque to detectable electromagnetic energy and to visible light, said sheet material being adherable uniformly to a body surface having a pronounced bulge to cover the entire surface for examination of said body surface by electromagnetic radiation in at least two different planes, whereby the pictures produced localize a body mass by position coordinates by reference to said grid lines in different planes.

12. Apparatus for use in localizing body masses and controlling biopsy or biopsy surgery according to claim 11 additionally including a box-like apparatus with walls on four sides of durable material transparent to said electromagnetic radiation, and openings on two opposing sides, and perforated by holes on all walled sides applyable over said grid sheet to hold the same in position against motion.

13. Apparatus for use in localizing body masses and controlling biopsy or biopsy surgery according to claim 11 additionally including a linear hollow stylet of material opaque to electromagnetic radiation and visible to light, having calibrating markings throughout the entire length, and perforated laterally to permit passage of a biopsy needle for insertion through a body surface covered with said grid sheet, whereby the examination of said body surface by electromagnetic radiation in at least two different planes, whereby the images produced localize a body mass by position coordinates by reference to said grid lines in different planes and in reference to said stylet.

14. Apparatus for use in localizing body masses and controlling biopsy or biopsy surgery according to claim 13 additionally including a biopsy needle insertable through one of said stylet perforations to place the needle accurately in relation to the body surface being examined.

* * * * *